| (12) | United States Patent | (10) Patent No.: | US 10,640,431 B2 |
|---|---|---|---|
| | Peters et al. | (45) Date of Patent: | May 5, 2020 |

(54) FERTILIZER MIXTURE CONTAINING NITRIFICATION INHIBITOR

(71) Applicant: EUROCHEM AGRO GMBH, Mannheim (DE)

(72) Inventors: Nils Peters, Frankenthal (DE); Reinhardt Haehndel, Limburgerhof (DE)

(73) Assignee: EuroChem Agro GmbH, Manheim (DE)

( * ) Notice: Subject to any disclaimer, the term of this patent is extended or adjusted under 35 U.S.C. 154(b) by 286 days.

(21) Appl. No.: 15/103,827

(22) PCT Filed: Dec. 12, 2014

(86) PCT No.: PCT/EP2014/077570
§ 371 (c)(1),
(2) Date: Nov. 3, 2016

(87) PCT Pub. No.: WO2015/086823
PCT Pub. Date: Jun. 18, 2015

(65) Prior Publication Data
US 2017/0050894 A1    Feb. 23, 2017

(30) Foreign Application Priority Data

Dec. 13, 2013 (DE) .................. 10 2013 020 588

(51) Int. Cl.
  C05G 3/08        (2006.01)
  C07D 231/12      (2006.01)
  C05C 3/00        (2006.01)
  C05C 1/02        (2006.01)
  C09K 15/20       (2006.01)

(52) U.S. Cl.
  CPC .............. C05G 3/08 (2013.01); C05C 1/02 (2013.01); C05C 3/005 (2013.01); C07D 231/12 (2013.01); C09K 15/20 (2013.01); Y02P 60/218 (2015.11)

(58) Field of Classification Search
  CPC .... C05G 3/08; C05G 3/00; C05C 1/02; C05C 3/005; C05C 1/00; C09K 15/20; C07D 231/12; Y02P 60/218; C05B 7/00; A01C 21/00
  See application file for complete search history.

(56) References Cited

U.S. PATENT DOCUMENTS

| 4,530,714 A | 7/1985 | Kolc et al. |
| 5,770,771 A | 6/1998 | Sulzer et al. |
| 5,951,736 A | 9/1999 | Grabarse et al. |
| 5,972,064 A | 10/1999 | Rittinger et al. |
| 6,066,190 A | 5/2000 | Grabarse et al. |
| 6,139,596 A | 10/2000 | Barth et al. |
| 6,488,734 B1 | 12/2002 | Barth et al. |
| 2010/0206030 A1 | 8/2010 | Whitehurst et al. |
| 2012/0252668 A1* | 10/2012 | Gewehr ............ A01N 25/00 504/101 |
| 2014/0037570 A1 | 2/2014 | Whitehurst et al. |
| 2014/0174140 A1 | 6/2014 | Oritz-Suarez et al. |
| 2015/0101379 A1 | 4/2015 | Gabrielson et al. |
| 2015/0148231 A1* | 5/2015 | Nave ............... A01N 25/00 504/101 |
| 2017/0050894 A1 | 2/2017 | Peters et al. |

FOREIGN PATENT DOCUMENTS

| BY | 4281 C1 | 3/2002 |
| CN | 102260123 A | 11/2011 |
| CN | 102557838 A | 7/2012 |
| DE | 19631764 A1 | 2/1998 |
| DE | 10164103 C1 | 1/2003 |
| DE | 10164104 C1 | 6/2003 |
| DE | 102005015362 A1 | 11/2005 |
| DE | 102007062614 A1 | 6/2009 |
| EP | 0119487 A1 | 9/1984 |
| EP | 0236972 A2 | 9/1987 |
| EP | 1120388 A1 | 8/2001 |
| EP | 0917526 B1 | 12/2001 |
| EP | 1182220 A1 | 2/2002 |
| EP | 1820788 A1 | 8/2007 |
| EP | 3029011 A1 | 6/2016 |
| RU | 2043026 C1 | 9/1995 |
| WO | WO-96/24566 A1 | 8/1996 |
| WO | WO-00/58317 A1 | 10/2000 |
| WO | WO-00/61522 A1 | 10/2000 |
| WO | WO-01/87898 A2 | 11/2001 |
| WO | WO-02/083697 A1 | 10/2002 |
| WO | WO-2006/010389 A1 | 2/2006 |
| WO | WO-2009/079994 A2 | 7/2009 |
| WO | WO-2011/032904 A1 | 3/2011 |
| WO | WO-2013/121384 A2 | 8/2013 |

(Continued)

OTHER PUBLICATIONS

Aurepio. "Calcium Ammonium Nitrate." <www.aurepio.pl/en/nitrogen-fertilizers/calcium-ammonium-nitrate-s251> pp. 1-2 (Aug. 11, 2013).*
International Search Report for International Application No. PCT/EP2016/064408, dated Sep. 16, 2016 (5 pages).
Abd El Halim et al., "3-[2-(3,5-dimethylpyrazolyl)] succinic anhydride: synthone for the synthesis of some heterocycles with potential pharmaceutical activity," Monatshefte für Chemie 125:1437-42 (1994).
Caplus Accession for XP-002741584 (1 page).
International Search Report and Written Opinion for International Application No. PCT/EP2014/077570, dated Jul. 27, 2015 (29 pages).
English translation of an Office Action for Chinese Application No. 201480074744.6, dated Nov. 30, 2018 (8 pages).

(Continued)

*Primary Examiner* — Jennifer A Smith
(74) *Attorney, Agent, or Firm* — Clark & Elbing LLP

(57) ABSTRACT

The invention features a fertilizer mixture containing
  (i) a calcium ammonium nitrate mineral fertilizer and (ii) 2-(N-3,4-dimethylpyrazole)succinic acid, or a salt thereof.

8 Claims, No Drawings

(56) References Cited

FOREIGN PATENT DOCUMENTS

WO    WO-2014/053401 A2    4/2014
WO    WO-2016/207210 A1    12/2016

OTHER PUBLICATIONS

Barth et al., "Effectiveness of 3,4-dimethylpyrazole phosphate as nitrification inhibitor in soil as influenced by inhibitor concentration, application form, and soil matric potential," Pedosphere. 18(3):378-85 (2008).
Di et al., "Inhibition of ammonium oxidation by a liquid formulation of 3,4-dimethylpyrazole phosphate (DMPP) compared with a dicyandiamide (DCD) solution in six new Zealand grazed grassland soils," J Soils Sediments 11(6):1032-9 (2011).
International Preliminary Report on Patentability for International Application No. PCT/EP2018/052200, dated Jan. 3, 2019 (9 pages).
International Search Report for International Application No. PCT/EP2018/052200, dated Apr. 26, 2018 (7 pages).
Zerulla et al., "3,4-dimethylpyrazole phosphate (DMPP)—a new nitrification inhibitor for agriculture and horticulture," Biol Fertil Soils. 34(2):79-84 (2001).
Notice of Allowance for Belarus Application No. 20160269, dated Jan. 21, 2020 (4 pages) (no English language translation provided).

* cited by examiner

FERTILIZER MIXTURE CONTAINING NITRIFICATION INHIBITOR

The invention relates to fertilizer mixtures comprising 2-(N-3,4-dimethylpyrazole)succinic acid (isomer mixture of 2-(3,4-dimethyl-1H-pyrazol-1-yl)succinic acid and 2-(2,3-dimethyl-1H-pyrazol-1-yl)succinic acid, in a ratio of preferably about 80:20, also referred to as DMPSA, or one of the individual compounds) and based on calcium ammonium nitrate (CAN) mineral fertilizer, and also to a process for preparing DMPSA.

In order to provide plants in agriculture with the nitrogen they need, fertilizers comprising ammonium compounds are frequently used.

Ammonium compounds are converted microbially to nitrate (nitrification) in the soil within a relatively short time. Nitrate, however, can be leached from the soil. The leached fraction is no longer available for plant nutrition, and so for this reason rapid nitrification is undesirable. In order to exploit the fertilizer more effectively, therefore, nitrification inhibitors are added to it. One known group of nitrification inhibitors are pyrazole compounds.

One problem attending the use of pyrazole compounds as nitrification inhibitors is their high volatility. When fertilizer preparations containing pyrazole compounds are stored, therefore, there is a continuous loss of active ingredient as a result of evaporation. For this reason the pyrazole compounds must be formulated in a nonvolatile form by means of appropriate measures.

EP-B-1 120 388 describes phosphoric acid addition salts of 3,4-dimethylpyrazole and 4-chloro-3-methylpyrazole for use as nitrification inhibitors. Through the salt form it is possible for the volatility to be significantly reduced.

WO 96/24566 relates to the use of low-volatility pyrazole derivatives having hydrophilic groups as nitrification inhibitors. As an example, 2-(N-3-methylpyrazole)succinic acid is proposed as a nitrification inhibitor. Suitable mineral fertilizers cited are ammonium-containing nitrates, sulfates or phosphates. The toxicity of this nitrification inhibitor makes it more difficult to use, particularly at relatively high concentrations.

WO 2011/032904 and WO 2013/121384 describe nitrification inhibitors one of which is DMPSA.

Nitrification inhibitors suitable for CAN fertilizers have not so far been disclosed, and so to date CAN fertilizers have been used without nitrification inhibitor.

It is an object of the present invention to provide a CAN fertilizer mixture which results in a low loss of nitrification inhibitor in the course of storage and application. A further object of the present invention is to provide an effective nitrification inhibitor for CAN, exhibiting a low volatility during storage and during application in the soil, and also corresponding CAN fertilizer mixtures. A further intention is to provide an improved process for the preparation of 2-(N-3,4-dimethylpyrazole)succinic acid.

The object is achieved in accordance with the invention by means of a fertilizer mixture comprising A. calcium ammonium nitrate mineral fertilizer which, besides ammonium nitrate and calcium carbonate and/or magnesium carbonate and optionally water, may contain up to 15 wt %, based on the calcium ammonium nitrate mineral fertilizer without water, of further ingredients, B. 100 to 10 000 ppm by weight, based on component A without water, of 2-(N-3,4-dimethylpyrazole)succinic acid.

The water fraction in component A and in the fertilizer mixture is preferably not more than 1.0 wt %, more preferably not more than 0.5 wt %, more particularly not more than 0.3 wt %, and is therefore negligible in the balance of quantities. Components A and B preferably make up at least 90 wt %, more preferably at least 95 wt %, of the fertilizer mixture.

Besides ammonium nitrate, the mineral fertilizer may comprise calcium carbonate or magnesium carbonate, or a mixture of calcium carbonate with magnesium carbonate.

Here and in the text below, quantity figures, particularly of the nitrification inhibitor, are based preferably on the solid mineral fertilizer A, even if water is additionally present, such as in liquid formulations, for example.

The invention further relates to a process for producing a fertilizer mixture of this kind by introducing 2-(N-3,4-dimethylpyrazole)succinic acid into the calcium ammonium nitrate mineral fertilizer and/or applying 2-(N-3,4-dimethylpyrazole)succinic acid to the calcium ammonium nitrate mineral fertilizer.

The invention further relates to a process for fertilizing soils exploited agriculturally or horticulturally, characterized in that a fertilizer mixture comprising A. calcium ammonium nitrate mineral fertilizer which, besides ammonium nitrate and calcium carbonate and/or magnesium carbonate and optionally water, may contain up to 15 wt %, based on the calcium ammonium nitrate mineral fertilizer without water, of further ingredients, B. 100 to 10 000 ppm by weight, based on component A without water, of 2-(N-3,4-dimethylpyrazole)succinic acid, or components A and B separately, but within a period of 0 to 5 hours, preferably 0 to 1 hour, more preferably approximately at the same time, is applied to the soils.

The invention further relates to a process for preparing 2-(N-3,4-dimethylpyrazole)succinic acid by reaction of 3,4-dimethylpyrazole with maleic acid and/or maleic anhydride in the absence of organic solvents or diluents, and subsequent crystallization from the resulting reaction product in the absence of organic solvents or diluents.

In this context, the following processes may be excluded or excepted:

"In the first experiment, 41.608 mol of maleic anhydride with a purity of more than 99.5% were introduced and dissolved in 11 liters of distilled water. The temperature rose here by 10° C. Then 41.608 mol of 80% strength aqueous 3,4-dimethylpyrazole solution (according to NMR spectrum, the solution of 3,4-DMP used contained approximately 2% of otherwise uncharacterized impurities) were added, the temperature rising by a further 12° C. After the end of the addition, the reaction mixture was heated to an internal temperature of 100° C. When this temperature was reached, the reaction mixture was stirred at 100° C. for 24 hours and then cooled. When the reaction mixture had cooled to 90° C., a sample was taken for NMR-spectroscopic reaction monitoring, and the reaction mixture was subsequently seeded with 1 g of product (crystals of 2-(N-3,4-dimethylpyrazole)succinic acid). At this temperature, crystallization did not yet begin, but the added crystals also no longer dissolved. On further cooling, crystallization began slowly from around 85° C. The major quantity of the product only crystallized at just below 80° C., with an increase in temperature. For complete crystallization, the reaction mixture was left to cool overnight with stirring. The precipitated solid was filtered off on three 8 L G3 glass suction filters, using a suction flask and membrane pump, under reduced pressure, and the solid product was washed with a total of 8 liters of distilled water and then dried under reduced pressure at a bath temperature of 60° C. The dry product thus obtained was placed into a container and mixed thoroughly, and a sample thereof was analyzed by NMR spectroscopy. In the subsequent experiments, instead of the distilled water, a corresponding amount of the combined filtrates was employed as the reaction medium. The excess amount of the combined filtrates was discarded."

These excluded or excepted processes, however, may also be an inventive alternative to the process of the invention with exclusion/exception.

The invention further relates to an aqueous solution of 2-(N-3,4-dimethylpyrazole) succinic acid having a pH of greater than 7.

2-(N-3,4-Dimethylpyrazole)succinic acid is preferably an isomer mixture of 2-(3,4-dimethyl-1H-pyrazol-1-yl)succinic acid and 2-(2,3-dimethyl-1H-pyrazol-1-yl)succinic acid, preferably in a molar ratio of 5:95 to 95:5, more preferably 50:50 to 95:5, more particularly 70:30 to 90:10.

It may be present in the acid form or in wholly or partly neutralized form or wholly or partly in salt form, as for example as alkali metal salt, such as potassium salt. The term "2-(N-3,4-dimethylpyrazole)succinic acid" used in accordance with the invention also includes the partly or fully neutralized or salt form.

It has been found in accordance with the invention that the combination of 2-(N-3,4-dimethylpyrazole)succinic acid with calcium ammonium nitrate mineral fertilizers results in an effective nitrification inhibitor which exhibits reduced volatility and a reduced loss during storage and also after application to the soil.

Furthermore, 2-(N-3,4-dimethylpyrazole)succinic acid has been found as a particularly effective nitrification inhibitor with low volatility and low toxicity. The present invention therefore relates accordingly to the specific combination of 2-(N-3,4-dimethylpyrazole)succinic acid with calcium ammonium nitrate fertilizers.

2-(N-3,4-Dimethylpyrazole)succinic acid may be prepared by any suitable methods, which are described for example in the general form in WO 96/24566. Preparation is accomplished preferably by reaction of 3,4-dimethylpyrazole with maleic acid or maleic anhydride. This reaction is typically carried out in an acidic environment. For the preparation of 3,4-dimethylpyrazole, reference may be made to Noyce et al., Jour. of Org. Chem. 20, 1955, pages 1681 to 1682. Reference may further be made to EP-A-0 474 037, DE-A-3 840 342, and EP-A-0 467 707, and also to EP-B-1 120 388. For the purification of the 3,4-dimethylpyrazole, reference may be made to DE-A-10 2009 060 150.

The reaction is performed favorably at temperatures from 0 to 150° C., preferably 50 to 120° C., more particularly 70 to 105° C., under atmospheric pressure in the absence of a solvent or, preferably, in an inert solvent, such as water, acetonitrile or dimethyl sulfoxide. Other suitable solvents are alcohols, ethers, ketones, water, and alkanes. Reaction in an organic acid such as acetic acid may also be appropriate. The product can be purified by recrystallization, by being taken up in diethyl ether, for example.

Maleic anhydride can be dissolved in water and reacted to give maleic acid. In that case an aqueous solution of 3,4-dimethylpyrazole can be added. The reaction may take place, for example, at temperatures of around 100° C., for example at 70 to 105° C. Since 3,4-dimethylpyrazole undergoes tautomerization under the reaction conditions in which the reaction is customarily carried out, or the 3,5-tautomerism of the pyrazole ring is eliminated by the substitution on the nitrogen, it is generally not possible to avoid the presence of isomer mixtures of the resulting substituted succinic acid, these mixtures featuring structural isomers.

More preferably the 2-(N-3,4-dimethylpyrazole)succinic acid is prepared by reaction of 3,4-dimethylpyrazole with maleic acid, maleic anhydride or maleic acid/maleic anhydride mixtures in the absence of organic solvents or diluents, and subsequent crystallization from the resulting reaction product in the absence of organic solvents or diluents. Where the reaction product is not in solution after the reaction, it is dissolved in a nonorganic solvent prior to crystallization.

In accordance with the invention it has been found that the product is obtained in high yield and purity if the accompanying use of organic solvents or diluents during the preparation and crystallization is avoided.

The presence of small amounts of organic solvents or diluents during the reaction or crystallization can be tolerated in this case. In accordance with the invention up to 10 wt %, more preferably up to 5 wt %, more particularly up to 2.5 wt % of organic solvents or diluents can be tolerated, based on nonorganic solvents or diluents used in the process. With particular preference no organic solvents or diluents at all are used in the reaction and crystallization. As a result of this, the process becomes particularly eco-friendly.

The reaction is carried out preferably in water as solvent, and the crystallization takes place from the (dissolved) aqueous reaction product.

Here it is possible to react aqueous solutions or pastes of 3,4-dimethylpyrazole and/or maleic acid and/or maleic anhydride. With particular preference both 3,4-dimethylpyrazole and maleic acid (anhydride) are used as aqueous solutions or pastes. Certain compounds may also be used as solids. For example, 3,4-DMP may also be used as a solid.

The crystallization preferably takes place by cooling of the aqueous reaction product. Here it is possible for seed crystals to be used as well, in order to initiate crystallization.

The reaction and crystallization may be carried out continuously or discontinuously. One or more reactors and/or crystallizers may be used. For example, a cascade of reactors and/or crystallizers may be used. Batchwise reaction is possible, as are semicontinuous or continuous reaction and crystallization.

The 2-(N-3,4-dimethylpyrazole)succinic acid obtained after the crystallization preferably has a purity of at least 99.7%, more preferably of at least 99.9%. This purity is preferably achieved even after the first crystallization.

As a result of preparation in accordance with the invention, a high yield and a high purity can be achieved with little cost and inconvenience. In particular, the use of expensive organic solvents and diluents which are potentially harmful to health and the environment is unnecessary. Nor is there any need for solvents to be removed or exchanged.

Through the use of the reaction product of 3,4-dimethylpyrazole with maleic acid, the volatility of the 3,4-dimethylpyrazole can be greatly lowered.

Application of the 2-(N-3,4-dimethylpyrazole)succinic acid as nitrification inhibitor for CAN fertilizer takes place according to the generally customary processes: the acid may be applied, for example, in solid form to the soil directly, in combination with CAN fertilizers in the form of power or granules. Moreover, it may be added to liquid CAN fertilizers, in a form, for example, in solution in water, also for the purpose of nitrogen stabilization, or may be applied together with such fertilizers, in dissolved form. Also possible is separate but closely timed application of DMPSA and CAN fertilizer.

It has proven particularly appropriate to use mixtures of 2-(N-3,4-dimethylpyrazole)succinic acid with a CAN mineral fertilizer. Fertilizer mixtures of this kind contain preferably 100 to 10 000 ppm by weight, based on the mineral fertilizer, of nitrification inhibitor (0.01 to 1 wt %), more preferably 0.03 to 0.5 wt %, more particularly 0.05 to 0.2 wt %.

The fertilizer mixtures may also include small amounts of water, as for example 0.1 to 0.5 wt %, based on the fertilizer mixture, including water. Large amounts of water in the fertilizer mixture ought to be avoided.

Having proven particularly appropriate on account of their good long-term activity are fertilizer mixtures produced according to the following method:

granules of mineral fertilizers, preferably calcium ammonium nitrate mineral fertilizers, are coated or impregnated with 2-(N-3,4-dimethylpyrazole)succinic acid by being sprayed with a solution of the nitrification inhibitor and dried again. The method is known, for example, from DE-A-41 28 828, hereby referenced in full. The sealing of the impregnated granules with a paraffin wax, which is an additional proposal in the latter document, is generally unnecessary, owing to the substantially lower volatility of the nitrification inhibitor of the invention.

The 2-(N-3,4-dimethylpyrazole)succinic acid may also be added during the actual production of the mineral fertilizer, in the slurry, for example.

If necessary, the mineral fertilizer may also be treated with polyacids, as described in WO 98/05607/EP-B-0 971 526.

The nitrification inhibitors are customarily applied to the soil in amounts of 100 g/ha to 10 kg/ha.

Application in liquid fertilizer formulations may be accomplished, for example, by fertigation with or without excess water, as described in DE-C-102 30 593.

In the context of its use as a nitrification inhibitor, the 2-(N-3,4-dimethylpyrazole)succinic acid, which can be prepared in a simple way from inexpensive starting products, is notable in particular for the fact that it effectively inhibits the nitrification of ammonium nitrogen in the soil over a long period of time.

A further factor is that this compound possesses favorable toxicological properties, has a low vapor pressure, and is sorbed well in the soil. A consequence of this is that 2-(N-3,4-dimethylpyrazole)succinic acid neither is emitted to the atmosphere by sublimation to any significant extent, nor is easily leached by water. As a result, first of all, economic advantages arise, such as high profitability in view of the longer-lasting effect of the nitrification inhibitor, and, moreover, environmental advantages such as a reduction in the burdening of air (climate gas-reducing) and of surface waters and groundwater. In the soil, the speed with which 2-(N-3,4-dimethylpyrazole)succinic acid diffuses is similar to that of nitrate or ammonium, and it can therefore act optimally. In the most general form, any desired suitable mineral fertilizers may be used in accordance with the invention. These are fertilizers containing ammonium or urea. Examples of such ammonium-containing fertilizers are NPK fertilizers, calcium ammonium nitrate, ammonium sulfate nitrate, ammonium sulfate, or ammonium phosphate.

The quantity figures below relate to the mineral fertilizer, preferably without water.

Particularly preferred in accordance with the invention is a combination of 2-(N-3,4-dimethylpyrazole)succinic acid with calcium ammonium nitrate mineral fertilizer. The latter comprises ammonium nitrate and calcium carbonate and/or magnesium carbonate as principal constituents, and water according to the degree of moisture. It is possible in accordance with the invention for the calcium ammonium nitrate mineral fertilizer to be able to contain up to 15 wt %, preferably up to 10 wt %, more preferably up to 5 wt %, based on the calcium ammonium nitrate mineral fertilizer without water, of further ingredients. Further ingredients are for example trace elements, further minerals, standardizers, binders, and so on.

The nitrogen content of component A (without water) is preferably 20 wt %, more preferably at least 22 wt %, very preferably 25 to 29 wt %, more particularly 26 to 28 wt %. Calcium ammonium nitrate comprises frequently 26 to 27 wt % of nitrogen, in which case, for example, there may be 13.5 wt % of fast-acting nitrate nitrogen and 13.5 wt % of slow-acting ammonium nitrogen.

The calcium content of component A (without water), when using calcium carbonate and ammonium nitrate as ingredients, is preferably 6 to 15 wt %, more preferably 7 to 13 wt %, more particularly 7 to 11 wt %. Approximately 10 wt % is a typical content.

When magnesium is used instead of calcium in the carbonate, a corresponding amount of Mg may preferably be present.

According to one preferred embodiment, when using calcium carbonate and ammonium nitrate as ingredients, component A may comprise 0.5 to 7 wt %, preferably 1 to 5 wt %, more preferably 3 to 5 wt %, based on component A without water, of MgO and/or Mg salt such as magnesium carbonate. Typically here MgO or $MgCO_3$ is used.

Furthermore, according to one embodiment of the invention, based on component A without water, component A may comprise 0.1 to 1 wt %, preferably 0.1 to 0.5 wt %, more particularly 0.15 to 0.3 wt % of boron as element and/or in the form of boron compounds.

For a description of calcium ammonium nitrate, one possible reference source is the definition in the EU Fertilizers Regulation 2003/2003.

Calcium ammonium nitrate is a white to gray solid which is normally odorless. The pH of a 10% strength aqueous solution is typically more than 4.5. The melting point is situated typically in the range from 160 to 170° C., depending on moisture content. The relative density is customarily 0.93 to 1.4 kg/l. The salt is hygroscopic and absorbs atmospheric moisture.

Calcium ammonium nitrate customarily has a water content of 0.1 to 0.5 wt %, preferably 0.1 to 0.2 wt %, more particularly about 0.15 wt %. As a result of the application of an aqueous solution of 2-(N-3,4-dimethylpyrazole)succinic acid to the calcium ammonium nitrate mineral fertilizer, this water content may more than double. It may consequently be necessary for the calcium ammonium nitrate mineral fertilizer thus treated to be dried after the nitrification inhibitor has been applied or incorporated.

Preference is given to using the 2-(N-3,4-dimethylpyrazole)succinic acid as an aqueous solution having a pH of greater than 7, more preferably greater than 10, more particularly greater than 12. As a result of the basic pH, the nitrification inhibitor is stabilized on the fertilizer mixture. The pH may be adjusted, for example, by addition of a base, more particularly an alkali metal hydroxide, such as NaOH or KOH.

Furthermore, it has been found in accordance with the invention that an aqueous solution of 2-(N-3,4-dimethylpyrazole)succinic acid having a pH of greater than 7, more preferably greater than 10, more particularly greater than 12, is more stable, allowing the production of highly concentrated aqueous solutions. The fraction of 2-(N-3,4-dimethylpyrazole)succinic acid, based on the aqueous solution, may thus amount preferably to 20 to 40 wt %, more preferably 25 to 35 wt %, more particularly 27.5 to 32.5 wt %.

It has been further found in accordance with the invention that, by adding one or more phosphates or polyphosphates to the aqueous solution, the water fraction of the aqueous solution can be reduced and the stability of the aqueous solution of the nitrification inhibitor can be further improved. Preferably, therefore, the aqueous solution contains 0.5 to 20 wt %, more preferably 1 to 10 wt %, more particularly 1.5 to 7 wt %, based on the aqueous solution, of one or more phosphates or polyphosphates.

Examples of phosphates contemplated are $Na_2HPO_4$, $Na_3PO_4$, $K_2HPO_4$, $K_3PO_4$, diammonium phosphate or calcium ammonium phosphate.

The invention also relates to the above-described aqueous solutions of 2-(N-3,4-dimethylpyrazole)succinic acid having a pH of greater than 7, and also to the preferred solutions with the stated fraction of nitrification inhibitor and more preferably phosphates or polyphosphates.

The invention is elucidated in more detail by the examples below:

EXAMPLES

A. Preparation Examples

Example 1

9.6 g of 3,4-dimethylpyrazole (0.1 mol) and 9.8 g of maleic anhydride (0.1 mol) were heated to 100° C. in 50 ml of 50% strength acetic acid. After 16 hours the reaction mixture was evaporated to dryness. When the residue is taken up in diethyl ether, the product (2-(N-3,4-dimethylpyrazole)succinic acid) is precipitated in pure form and is isolated by filtration: white crystals in a yield of 92%. In the NMR spectrum there are a number of methyl signals apparent, this being in agreement with the elimination of the 3,5-tautomerism as a result of the substitution on nitrogen.

Example 2

Preparation on the 200 kg Scale

Starting materials used for the experiments were maleic anhydride from CVM with a purity of more than 99.5%, and an 80% strength aqueous solution of 3,4-dimethylpyrazole (3,4-DMP) from BASF SE. According to NMR spectrum, the solution of 3,4-DMP used contained about 2% of otherwise uncharacterized impurities.

The experiments were first conducted in a 20 L reaction vessel, which in further experiments was replaced by a 25 L reaction vessel.

In the first experiment, 41.608 mol of maleic anhydride were introduced and dissolved in 11 liters of distilled water. The temperature rose here by 10° C. Then 41.608 mol of 80% strength aqueous 3,4-dimethylpyrazole solution were added, the temperature rising by a further 12° C. After the end of the addition, the reaction mixture was heated to an internal temperature of 100° C. When this temperature was reached, the reaction mixture was stirred at 100° C. for 24 hours and then cooled. When the reaction mixture had cooled to 90° C., a sample was taken for NMR-spectroscopic reaction monitoring, and the reaction mixture was subsequently seeded with 1 g of product (crystals of 2-(N-3,4-dimethylpyrazole)succinic acid). At this temperature, crystallization did not yet begin, but the added crystals also no longer dissolved. On further cooling, crystallization began slowly from around 85° C. The major quantity of the product only crystallized at just below 80° C., with an increase in temperature. For complete crystallization, the reaction mixture was left to cool overnight with stirring. The precipitated solid was filtered off on three 8 L G3 glass suction filters, using a suction flask and membrane pump, under reduced pressure, and the solid product was washed with a total of 8 liters of distilled water and then dried under reduced pressure at a bath temperature of 60° C. The dry product thus obtained was placed into a container and mixed thoroughly, and a sample thereof was analyzed by NMR spectroscopy. In the subsequent experiments, instead of the distilled water, a corresponding amount of the combined filtrates was employed as the reaction medium. The excess amount of the combined the bifiltrates was discarded.

NMR-spectroscopic reaction monitoring after 24 hours showed a relatively constant conversion of around 92%, with a relatively constant P1/P2 (2-(3,4-dimethyl-1H-pyrazol-1-yl)succinic acid/2-(2,3-dimethyl-1H-pyrazol-1-yl) succinic acid) isomer ratio of around 3.3. Only at the start of the serial experiment was the ratio slightly higher. That, however, was also anticipated, since the use of the filtrate instead of the distilled water as reaction medium introduced a greater amount of P2 (P1/P2 ratio in the filtrates is around 1.0) into the subsequent experiments.

After just a few experiments, the composition of the reaction mixture after a reaction time of 24 hours reached constant levels. By the same token, the compositions of the isolated products from the individual experiments differ only slightly from one another.

The solids, obtained on average with a yield of 90.22%, possessed a purity of 99.9% and on average an isomer ratio of 4.0 (2-(3,4-dimethyl-1H-pyrazol-1-yl)succinic acid to 2-(2,3-dimethyl-1H-pyrazol-1-yl)succinic acid). Impurities of 3,4-DMP, maleic acid, and rac-malic acid were detectable in the 1H NMR spectra not at all or only in traces (<0.1%).

Example 3

The carrier fertilizer used was calcium ammonium nitrate with 27% N and 10% Ca. 2 g of 2-(N-3,4-dimethylpyrazole) succinic acid and 46 g of KOH were dissolved in 133 g of water. 20 kg of the carrier fertilizer in the form of granules were slowly sprayed in a drum with 85 g of the formulation of the pyrazole compound.

Example 4

Example 3 was repeated, using 111 g of water and 22 g of diammonium phosphate instead of 133 g of water.

Comparative Example

In analogy to example 3, 3,4-dimethylpyrazole phosphate (DMPP) was used instead of 2-(N-3,4-dimethylpyrazole) succinic acid.

B. Application Examples

Example 1

Investigation of Storage Stability

Calcium ammonium nitrate (CAN) mineral fertilizer additized with 2-(N-3,4-dimethylpyrazole)succinic acid (DMPSA) or with DMPP, in accordance with example 3 or comparative example, respectively, was investigated for storage stability in an accelerated test, in which the nitrification-inhibited mineral fertilizers were stored in an open glass beaker (which, as a mini-heap, mimics the storage situation in a large heap) for 40 days at 30° C., 40% to 50% relative humidity and approximately 1.2 m/s air speed in an aerated heating cabinet. The concentration of nitrification inhibitor on the mineral fertilizer was determined before, during and after storage at two different depths in the bed, and the loss of nitrification inhibitor was ascertained. In each case about 10 to 30 g of treated mineral fertilizer were stored. The concentration of DMPP at the start was 1.028 g/kg fertilizer; for 2-(N-3,4-dimethylpyrazole)succinic acid, the figure was 1.244 g/kg fertilizer.

After 20 and 40 days, samples were taken from a surface region of the fertilizer bed (0 to 5 cm sampling depth and >5 cm sampling depth).

The results are shown in table 1 below, where DMPSA denotes 2-(N-3,4-dimethylpyrazole)succinic acid.

TABLE 1

Storage stability of DMPP and DMPSA on CAN

| | Analytical value [g/kg] |
|---|---|
| DMPP on CAN | |
| Value at start | 1.028 |
| d20, 0-5 cm | 0.86 |
| d20, >-5 cm | 0.91 |
| d40, 0-5 cm | 0.45 |
| d40, >-5 cm | 0.68 |
| DMPSA on CAN | |
| Value at start | 1.244 |
| d20, 0-5 cm | 1.15 |
| d20, >-5 cm | 1.18 |
| d40, 0-5 cm | 1.21 |
| d40, >-5 cm | 1.26 | d = day
0-5 cm sampling depth

From the table it is clear that the loss is much lower for 2-(N-3,4-dimethylpyrazole)succinic acid than for DMPP on storage over 20 to 40 days.

This is evidence of the advantages of the fertilizer of the invention.

Example 2

Verification of the Biological (Nitrification-Inhibiting) Effect of the 2-(N-3,4-Dimethylpyrazole)Succinic Acid The biological activity of 2-(N-3,4-dimethylpyrazole)succinic acid was tested in a number of field trials in different environments.

The field trials were set up, sampled, harvested, and evaluated in accordance with the processes customary in agricultural trialing.

The plant and soil samples were analyzed by standard methods. The other production-related measures, such as the crop protection, were in line with good agricultural practice and were carried out uniformly.

Preferably, a distinguishing feature of a biologically active nitrification inhibitor is that it exhibits higher levels of $NH_4$ nitrogen relative to the control (here, unadditized CAN carrier fertilizer) within a period of up to 4 weeks and longer after application. As a consequence of these conditions, the yield is increased and the nitrate content of the plants is reduced.

The active ingredient was applied in analogy to example 3 to solid CAN fertilizers with an application rate of 0.73% based on the reduced nitrogen. The active ingredient exhibits a strong nitrification-inhibiting action in the soil after application of the fertilizers. In the CAN (calcium ammonium nitrate)+DMPSA, given by way of example in table 2, there are still considerable amounts of reduced nitrogen both after 14 days and after 28 days, in comparison to untreated products; without nitrification inhibitor, the entire reduced nitrogen has undergone nitrification and conversion to nitrate N after no later than 28 days.

TABLE 2

Inhibition of nitrification by DMPSA

| | % $NH_4$ N (or $NH_2$ N) of the fertilized N after | | |
|---|---|---|---|
| Fertilizer | 0 days | 14 days | 28 days |
| CAN | 100 | 9.1 | 0.0 |
| CAN + DMPSA | 100 | 79.3 | 61.9 |

Example 3

Reduction in Greenhouse Gas Emissions ($N_2O$)

In addition to the protection of the hydrosphere, the maximum avoidance of release of climate-relevant gases as a consequence of the agricultural exploitation of soils is also a great challenge for agriculture.

The compilation of the measurements of nitrous oxide ($N_2O$), an extremely active climate gas (around 300 times stronger than $CO_2$), both during the vegetation period of winter wheat after fertilization, and after harvesting into the winter, gave a reduction by 28% (table 3) in comparison to conventional CAN when using CAN+DMPSA in accordance with example 3.

TABLE 3

Effect of fertilization with CAN with and without DMPSA on release of climate gas during winter wheat culture

| Without fertilization | CAN | CAN + DMPSA |
|---|---|---|
| g $N_2O$ N/ha cumulative March to December | | |
| 1149 | 2690 | 1953 |
| 43% | 100% | 72% |

Example 4

Effect on Yield and Quality of Agricultural and Horticultural Crops

Yields

In addition to possible consequences for the gentle treatment of soil, water, and air, the effect on yield and quality is particularly important to the farmer. The compilation of the weighed yields of various crops shows a consistently improved yield boost by the fertilizers with DMPSA in accordance with example 3 than by the use of the respective conventional fertilizers (table 4). Here there are virtually no differences between agricultural crops and vegetable crops, or in terms of the respective climate environments and different soils. The reasons for the extra yields are firstly the reduced losses as a result of leaching and the gaseous losses through denitrification, and secondly in the partial ammonium nutrition of the plants, which is beneficial for the plant metabolism by comparison with the customary nitrate nutrition with conventional fertilizers.

TABLE 4

Effect of fertilization with CAN with and without DMPSA on the yield of various garden and agricultural crops

| Crop | Region/Country | Fertilizer used | Yield dt/ha without | Yield dt/ha with | Extra yield [%] |
|---|---|---|---|---|---|
| Potato | Hanover/D | CAN | 464 | 609 | 31 |
| Potato | Jutland/DK | CAN | 390 | 405 | 32 |
| Potato | Picardy/F | CAN | 642 | 667 | 4 |
| Potato | Orgiano/I | CAN | 531 | 582 | 9 |
| Potato | Galicia/E | CAN | 644 | 728 | 13 |
| Celery* | Palatinate/D | CAN | 563 | 595 | 5 |
| Celery* | Palatinate/D | CAN | 756 | 781 | 3 |
| Chinese cabbage** | Palatinate/D | CAN | 757 | 842 | 11 |
| Chinese cabbage** | Palatinate/D | CAN | 817 | 930 | 13 |

*weight/100 plants
**weight per head, g

The invention claimed is:

1. A fertilizer mixture comprising:
   (a) as component A, a calcium ammonium nitrate mineral fertilizer which, besides ammonium nitrate and calcium carbonate and optionally water, may contain up to 15 wt %, based on the calcium ammonium nitrate mineral fertilizer without water, of further ingredients,
   (b) as component B, from 100 to 10 000 ppm by weight, based on component A without water, of a salt form of 2-(N-3,4-dimethylpyrazole)succinic acid.

2. The fertilizer mixture as claimed in claim 1, wherein the salt form of 2-(N-3,4-dimethylpyrazole)succinic acid is a di-alkali metal salt.

3. The fertilizer mixture as claimed in claim 2, wherein the di-alkali metal salt is a dipotassium salt.

4. The fertilizer mixture as claimed in claim 1, characterized in that in component A, based on the calcium ammonium nitrate mineral fertilizer without water, the nitrogen content is at least 22 wt %.

5. The fertilizer mixture as claimed in claim 1, characterized in that in component A, based on the calcium ammonium nitrate mineral fertilizer without water, the calcium content is 6 to 15 wt %.

6. The fertilizer mixture as claimed in claim 1, characterized in that component A contains 0.5 to 7 wt %, based on the calcium ammonium nitrate mineral fertilizer without water, of MgO, Mg salt, or mixtures thereof.

7. The fertilizer mixture as claimed in claim 1, characterized in that component A contains 0.01 to 1 wt %, based on the calcium ammonium nitrate mineral fertilizer without water, of boron as element or in the form of boron compounds.

8. A process for producing a fertilizer mixture as claimed in claim 1 by introducing the salt form of 2-(N-3,4-dimethylpyrazole)succinic acid into the calcium ammonium nitrate mineral fertilizer and/or applying the salt form of 2-(N-3,4-dimethylpyrazole)succinic acid to the calcium ammonium nitrate mineral fertilizer.

* * * * *